(12) United States Patent
Buchan (10) Patent No.: US 7,084,161 B2
(45) Date of Patent: Aug. 1, 2006

(54) METHOD FOR TREATING INFLAMMATORY DISEASES OR CONDITIONS

(75) Inventor: Kevin William Buchan, Stevenage (GB)

(73) Assignee: SmithKlineBeecham Corporation, Philadelphia, PA (US)

( * ) Notice: Subject to any disclaimer, the term of this patent is extended or adjusted under 35 U.S.C. 154(b) by 342 days.

(21) Appl. No.: 10/398,629

(22) PCT Filed: Oct. 1, 2001

(86) PCT No.: PCT/GB01/04373

§ 371 (c)(1),
(2), (4) Date: Aug. 21, 2003

(87) PCT Pub. No.: WO02/28434

PCT Pub. Date: Apr. 11, 2002

(65) Prior Publication Data

US 2005/0131035 A1    Jun. 16, 2005

(30) Foreign Application Priority Data

Oct. 5, 2000    (GB)    .................................. 0024361.8

(51) Int. Cl.
*A61K 31/425* (2006.01)
(52) U.S. Cl. ...................................... 514/365
(58) Field of Classification Search ..................... None
See application file for complete search history.

(56) References Cited

FOREIGN PATENT DOCUMENTS

| EP | 1 023 907 | 8/2000 |
|----|-----------|--------|
| WO | 97/28149  | 8/1997 |
| WO | 01/00603  | 1/2001 |

OTHER PUBLICATIONS

He T-C et al., "PPAR-Delta is an APC-Regulated Target of Nonsteroidal Anti-Inflammatory Drugs," *Cell*, vol. 99, No. 3, Oct. 12, 1999, pp. 335-345.

*Primary Examiner*—Phyllis G. Spivack
(74) *Attorney, Agent, or Firm*—Jennifer L. Fox

(57) ABSTRACT

A method of treating inflammatory diseases comprising administering 2-[2-methyl-4-[[[4-methyl-2-[4-(trifluoromethyl)phenyl]-1,3-thiazol-5-yl]methyl]sulfanyl]phenoxy]acetic acid is disclosed.

1 Claim, 3 Drawing Sheets

FIG. 1

EFFECTS OF COMPOUND A ON LPS-INDUCED iNOS ACTIVITY IN J774 MACROPHAGES

EFFECTS OF COMPOUND B ON LPS(1ug/ml)-INDUCED iNOS ACTIVITY IN J774 MACROPHAGES

FIG. 3

EFFECTS OF COMPOUND B ON LPS(1ug/ml)-INDUCED TNF PRODUCTION IN J774 CELLS

EFFECTS OF COMPOUND B ON LPS(1ug/ml)-INDUCED iNOS ACTIVITY IN J774 MACROPHAGES

METHOD FOR TREATING INFLAMMATORY DISEASES OR CONDITIONS

This application is filed pursuant to 35 U.S.C. § 371 as a United States National Phase Application of International Application No. PCT/GB01/04373 filed Oct. 1, 2001, which claims priority from 0024361.8 filed Oct. 5, 2000.

The present invention is concerned with medicaments. More particularly, the invention relates to compounds that bind to and activate PPAR delta. In another aspect, the present invention relates to methods for prevention or treatment of inflammatory diseases and conditions and methods for identifying compounds useful in the treatment of inflammatory diseases or conditions.

Peroxisome proliferator activated receptor (hereinafter referred to as PPAR) is a known member of the steroid/retinoid/thyroid hormone receptor family of ligand activated transcription factors and is activated, inter-alia, by high micromolar concentrations of certain peroxisome proliferators. Peroxisome proliferator activated receptor alpha (hereinafter referred to as PPARα), peroxisome proliferator activated receptor gamma (hereinafter referred to as PPARγ) and peroxisome proliferator activated receptor delta (hereinafter referred to as PPARδ) have respectively been identified as subtypes of PPARs.

Nitric oxide is the endogenous stimulator of the soluble guanylate cyclase enzyme and is involved in a number of biological actions. Excess nitric oxide production is also thought to be involved in a number of conditions, including many inflammatory diseases. The biochemical synthesis of nitric oxide from L-arginine is catalysed by the enzyme NO synthase. Many inhibitors of NO synthase have been described and proposed for therapeutic use, particularly those displaying selectivity for either inducible NO synthase (iNOS) or neuronal NO synthase (nNOS) over endothelial NO synthase (eNOS).

Tumor necrosis factor (TNF) is known to mediate many biological responses in vivo. Clinical and Pre-clinical studies in animals and humans with specific TNF neutralising antibodies, soluble TNF receptor constructs and TNF detection techniques have implicated TNF as a mediator in numerous pathologies including inflammatory/auto immune diseases or conditions.

The present inventors have surprisingly found that activators of the peroxisome proliferator activated receptor delta (hereinafter referred to as PPARδ inhibit INOS and TNF formation and are therefore useful in the prophylaxis and treatment of inflammatory diseases or conditions.

The present invention therefore provides the use of PPARδ activators in the treatment of inflammatory diseases or conditions and methods of treating inflammatory diseases or conditions employing PPARδ activators. More particularly, the present invention provides the use of potent and selective PPARδ agonists for use in the treatment of inflammatory diseases or conditions.

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation with regards to disease typically is referred to as chronic inflammation and can last up to a lifetime. Such chronic inflammation may manifest itself through disease symptoms. The aim of anti-inflammatory therapy is therefore to reduce this chronic inflammation and allow for the physiological process or heating and tissue repair to progress.

Examples of inflammatory diseases or conditions include those of the joint, particularly arthritis (e.g. rheumatoid arthritis, osteoarthritis, prosthetic joint failure), or the gastrointestinal tract (e.g. ulcerative colitis, Crohn's disease, and other inflammatory bowel and gastrointestinal diseases, gastritis and mucosal inflammation resulting from infection, the enteropathy provoked by non-steroidal anti-inflammatory drugs), of the lung (e.g. adult respiratory distress syndrome, asthma, cystic fibrosis, or chronic obstructive pulmonary disease), of the heart (e.g. myocarditis), of nervous tissue (e.g. multiple sclerosis), of the pancreas, (e.g. inflammation associated with diabetes melitus and complications thereof, of the kidney (e.g. glomerulonephritis), of the skin (e.g. dermatitis, psoriasis, eczema, urticaria, burn injury), of the eye (e.g. glaucoma) as well as of transplanted organs (e.g. rejection) and multi-organ diseases (e.g. systemic lupus erythematosis, sepsis) and inflammatory sequelae of viral or bacterial infections and inflammatory conditions associated with atherosclerosis and following hypoxic or ischaemic insults (with or without reperfusion), for example in the brain or in ischaemic heart disease.

Preferably, the PPAR delta activators are PPARδ agonists. As used herein, by "agonist", or "activating compound", or "activator", or the like, is meant those compounds which have a pKi of at least 6.0 to the relevant PPAR, for example human PPARδ, in the binding assay described below, and which achieve at least 50% activation of the relevant PPAR relative to the appropriate indicated positive control in the transfection assay described, for example in WO 00/08002 at concentrations of $10^{-5}$ M or less. More preferably, the compounds of this invention achieve 50% activation of human PPARδ in the transfection assay at concentrations of $10^{-7}$ M or less.

Most preferably, PPAR delta activators are selective hPPARδ agonists. As used herein, a "selective hPPARδ agonist" is a hPPARδ agonist whose EC50 for PPARδ is at least 10 fold lower than its EC50 for PPARλ and PPARα. Such selective compounds may be referred to as "10-fold selective". EC50 is defined in the transfection assay described, for example in WO 00.08002 and is the concentration at which a compound achieves 50% of its maximum activity. Most preferred compounds are greater than 100-fold selective hPPARδ agonists.

The following are further particular aspects of the present invention:

(a) a PPAR delta activator (e.g. a compound of formula (I)) for use as a therapeutic agent in the treatment of inflammatory diseases or conditions.

(b) pharmaceutical formulations comprising a PPAR delta activator (e.g. a compound of formula (I)) and at least one pharmaceutical carrier, wherein the PPAR delta agonist is present in an amount effective for use in the treatment of inflammatory diseases or conditions.

(c) the use of a PPAR delta activator (e.g. a compound of formula (I)) in the manufacture of a medicament for the treatment of inflammatory diseases or conditions.

(d) a method of treating inflammatory diseases or conditions in a mammal, such as a human, which comprises the administration of a therapeutically effective amount of a PPAR delta activator (e.g. a compound of formula (I)) to a said mammal.

The term 'treatment' as used herein includes prophylaxis as well as alleviation of established inflammatory diseases or conditions. The PPAR delta activators may be used as compounds or pharmaceutically acceptable derivatives thereof.

By pharmaceutically acceptable derivative is meant any pharmaceutically acceptable salt, solvate, ester or amide, or salt or solvate of such ester or amide, of the PPAR delta activator, or any other compound which upon administration to the recipient is capable of providing (directly or indirectly) the PPAR delta activator or an active metabolite or residue thereof.

Suitable PPAR delta activators are described for example in WO 01/00603 which discloses compounds of formula (I), and pharmaceutically acceptable salts and, solvates thereof,

A

B

C

For example, when n is 1, Y is S, Z is N, and $R^3$ is para-$CF_3$:

wherein:

X represents a COOH (or a hydrolysable ester thereof) or tetrazole group;

$X^1$ represents NH, $NCH_3$, O, S, a bond (i.e. is absent), $CH_2$, or CH where the dashed line indicates that when X1 is CH the depicted bond is a double bond;

$X^2$ represents O or S;

$R^1$ and $R^2$ independently represent H, $CH_3$, $OCH_3$, or halogen;

n is 1 or 2;

one of Y and Z is N and the other is S or O:

y is 0, 1, 2, 3, 4 or 5;

Each $R^3$ independently represents $CF_3$ or halogen.

These compounds may be conveniently prepared by a general process wherein a moiety like A is coupled to an alcohol (B) using the Mitsunobu protocol (O. Mitsunobu, 1981 Synthesis, p 1) or by alkylation of A using a suitable non nucleophilic base such as $K_2CO_3$, $Cs_2CO_3$ or NaH, with an alkyl halide (C). Note that this synthesis is preferably carried out with the acid group protected by R. Preferably, R is 1–6 alkyl which can be hydrolyzed off to give an acid of Formula (I), or if readily hydrolyzable, the resulting ester can be administered.

Intermediates of type A are commercially available. The synthesis of intermediates of type B is also illustrated below.

Furthermore, the tetrazole derivatives may be conveniently prepared by a general process wherein a moiety like D is coupled to an alcohol (B) using the Mitsunobu protocol (O. Mitsunobu, 1981 Synthesis, p 1), by alkylation of D using a suitable non nucleophilic base such as $K_2CO_3$, $Cs_2CO_3$ or NaH, with an alkyl halide (C) or by coupling of a moiety like E with an alkyl halide (C) using a suitable non nucleophilic base such as NaOH.

Preferred compounds of the invention are:
- 2-{2-methyl-4-[({4-methyl-2-[4-(trifluoromethyl)phenyl]-1,3-thiazol-5-yl}methyl)sulfanyl]phenoxy}acetic acid
- 2-{2-methyl-4-[({4-methyl-2-[4-(trifluoromethyl)phenyl]-1,3-oxazol-5-yl}methyl)sulfanyl]phenoxy}acetic acid
- methyl 2-{4-[({4-methyl-2-[4-(trifluoromethyl)phenyl]-1,3-thiazol-5-yl}methyl)sulfanyl]phenoxy}acetate
- 2{-4-[({4-methyl-2-[4-(trifluoromethyl)phenyl]-1,3-thiazol-5-yl}methyl)sulfanyl]phenoxy}acetic acid
- (E)-3-[2-methyl-4-({4-methyl-2-[4-(trifluoromethyl)phenyl]-1,3-thiazol-5-yl}methoxy)phenyl]-2-propenoic acid
- 2-{3-chloro-4-[({4-methyl-2-[4-(trifluoromethyl)phenyl]-1,3-thiazol-5-yl}methyl)sulfanyl]phenyl}acetic acid A particularly preferred PPAR delta agonist is {2-methyl-4-[4-methyl-2-(4-trifluoromethyl phenyl)thiazol-5-ylmethylthio]phenoxy}-acetic acid and pharmaceutically acceptable salts, solvates, and hydrolyzable esters thereof (formula (II) below).

(II)

It will also be appreciated by those skilled in the art that the PPAR delta activator may also be utilized in the form of a pharmaceutically acceptable salt or solvate thereof. The physiologically acceptable salts include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a PPAR delta activator include both compounds and their pharmaceutically acceptable salts and solvates.

The PPAR delta activators and their pharmaceutically acceptable derivatives are conveniently administered in the form of pharmaceutical compositions. Such compositions may conveniently be presented for use in conventional manner in admixture with one or more physiologically acceptable carriers or excipients. The carrier(s) must be "acceptable" in the sense of being compatible with the other ingredients of the formulation and not deleterious to the recipient thereof.

While it is possible that the PPAR delta activators may be therapeutically administered as the raw chemical, it is preferable to present the active ingredient as a pharmaceutical formulation.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation of insufflation administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch, polyvinylpyrrolidone) or hydroxymethyl cellulose or hydroxymethyl cellulose fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

For topical administration to the epidermis, the compounds may be formulated as creams, gels, ointments or lotions or as a transdermal patch.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For intranasal administration the compounds of the invention may be used, for example as a liquid spray, as a powder or in the form of drops.

For administration by inhalation the compounds according to the invention are conveniently delivered in the form of an aerosol spray presentation from pressurised packs or a nebuliser, with the use of a suitable propellant, e.g. 1,1,1,2-trifluoroethane (HFA 134A) and 1,1,1,2,3,3,3,-heptapropane (HFA 227), carbon dioxide or other suitable gas. In the case of a pressurised aerosol the dosage until may be determined by providing a valve to deliver a metered amount. Capsules and cartridges of e.g. gelatin for use in an inhaler or insufflator may be formulated containing a powder mix of a compound of the invention and a suitable powder base such as lactose or starch.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of the PPAR delta activator required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The PPAR delta activators for use in the instant invention may be used in combination with one or more other therapeutic agents for example, pain relievers such as a glycine antagonist, a sodium channel inhibitor (e.g. lamotrigine), a substance P antagonist (e.g. an NK1 antagonist), acetaminophen or phenacetin; a matrix metalloproteinase inhibitor; a nitric oxide synthase (NOS) inhibitor (e.g. an iNOS or an nNOS inhibitor); an inhibitor of the release, or action, of tumour necrosis factor α; an antibody therapy (e.g. a monoclonal antibody therapy); a stimulant, including caffeine; an H2-antagonist, such as ranitidine; a proton pump inhibitor, such as omeprazole; an antacid, such as aluminium or magnesium hydroxide; an antiflatulent, such as simethicone; a decongestant, such as phenylephrine, phenylprolpanolamine, pseudoephedrine, oxymetazoline, epinephrine, naphazoline, xylometazoline, propylhexedrine, or levo-desoxyephedrine; an antitussive, such as codeine, hydrocodone, carmiphen, carbetapentane, or dextramethorphan; a diuretic; or a sedating or non-sedating antihistamine; a COX-2 inhibitor such as Vioxx™ or Celebrex™ and other NSAIDs. The invention thus provides in a further aspect the use of a combination comprising a compound of formula (I) with a further therapeutic agent in the treatment of inflammation.

When the PPAR delta activators are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a PPAR delta activator is used in combination with a second therapeutic agent active against the same disease, the dose of each compound may differ from that when the compound is used alone. Appropriate doses will be readily appreciated by those skilled in the art.

The present inventors have found that, chemical compounds which are activators of PPAR delta are also inhibitors of the formation of iNOS and TNF which are implicated in inflammation. The identification of novel PPAR delta activators may lead to more effective drugs for the treatment of inflammation. Accordingly, the invention further provides a method for identifying compounds that will be useful in treating inflammation comprising the step of determining whether the compound interacts directly with PPAR delta, or the step of determining whether the compound activates PPAR delta. Suitable screening tests include the binding and transfection assays discussed hereinabove and disclosed in WO 00 08002. A suitable control for PPAR delta is for example 2-{2-methyl-4-[({4-methyl-2-[3-fluoro-4-(trifluoromethyl)phenyl]-1,3-thiazol-5-yl}methyl)sulfanyl]phenoxy}acetic acid which conveniently may be radiolabelled.

The present invention also provides a method for treating inflammatory diseases of conditions in a subject comprising the administration of therapeutically effective amounts of compounds identified using the method of the invention. The invention also provideds the use of a compound identified by a screening method of the invention in the manufacture of a medicament for the treatment of inflammatory diseases or conditions.

The following examples are set forth to illustrate the synthesis of some particular compounds of the present invention and to further exemplify particular applications of general processes described above. Accordingly, the following Example section is in no way intended to limit the scope of the invention contemplated herein.

EXAMPLES

Example 1

Preparation of 2-{2-methyl-4-[({4-methyl-2-[4-(trifluoromethyl)phenyl]-1,3-thiazol-5-yl}methyl)sulfanyl]phenoxy}acetic Acid Intermediate A

Chlorosulfonic acid (15 mL) was cooled to 0° C. then 10.0 g (0.05M) of ethyl (2-methylphenoxyacetate) was added over 10 min. The reaction mixture was stirred at 0–5° C. for 30 m, the bath was removed and stirring continued for 2 h. The reaction mixture was poured into ice, forming a white solid which was washed with ice water and dried under high vacuum affording the title compound (12.846 g, 86%).

Intermediate B:

To a well stirred solution of LiAlH$_4$ (1.52 g, 40 mmol) in dry THF (50 mL) at 0° C., was slowly added a solution of ethyl 4-methyl-2-[4-(trifluoromethyl)phenyl]-thiazole-5-carboxylate (12.6 g, 40 mmol) in dry THF (50 mL). The mixture was stirred at room temperature for 2 hs. The reaction was quenched by slow addition at 0° C. of water (2 mL), 5N NaOH (2 mL) and water (6 mL). The precipitate was filtered, washed with EtOAc, MeOH, CH$_2$Cl$_2$ and THF. After evaporation, a yellow solid was obtained, that was crystallyzed from MeOH-water to afford intermediate B depicted above (9.90 g, 36 mmol, 90%) as a yellow solid mp 120–122° C.

Intermediate C:

To a cold (0° C.) stirred solution of intermediate B (8.2 g, 30 mmol) and Et$_3$N (6.07 g, 8.36 mL, 60 mmol), in dry CH$_2$Cl$_2$ (120 mL) was slowly added MeSO$_2$Cl (5.49 g, 3.71 mL, 48 mmol). After 2 hs at 0° C. more Et$_3$N (6 mmol) and MeSO$_2$Cl (4.8 mmol) were added. After 2 more h a tic (hexane:EtOAc, 1:1) showed complete reaction. The reaction mixture was diluted with CH$_2$Cl$_2$ (120 mL) and washed with NaHCO$_3$ (sat.) (2×240 mL) and water (2×240 mL), dried, filtered and evaporated to afford intermediate C (8.0 g, 27 mmol, 90%) as a yellow solid.

2-{2-methyl-4-[({4-methyl-2-[4-(trifluoromethyl)phenyl]-1,3-thiazol-5-yl}methyl)sulfanyl]phenoxy}acetic Acid Intermediate A (4.68 g, 16 mM) was refluxed with 9.6 g of tin powder in ethanol (20 mL) and dioxane/HCl (20 mL). After 3 h the reaction mixture was poured into ice and CH$_2$Cl$_2$ (200 mL) and filtered. The phases were separated and the aqueous layer was extracted 2×50 mL CH$_2$Cl$_2$. The combined organic layers were dried (MgSO$_4$), filtered and evaporated to yield 3.5 g (97%). This material readily forms disulfides and therefore was used immediately. It was dissolved in acetonitrile (50 mL) with intermediate C (4.0 g, 14.0 mM) and Cs$_2$CO$_3$ (10.1 g, 31.0 mM) and stirred for 1 h then diluted with ether (200 mL) and water (200 mL). The phases were separated and the organic phase was washed 2× NaOH 0.1N (50 mL), dried (MgSO$_4$), filtered and evaporated to afford crude product (6.57 g,) which was slurried in hexane:ether (1:1) and filtered to yield pure intermediate D (5.0 g, 74%). This material was hydrolyzed as described below to prepare the title compound. A solution of the corresponding ester (Intermediate D) (1 mmol) in THF (10 mL) (in some cases few drops of MeOH were added to help solubility), was treated with 1N LiOH in water (2 mL, 2 mmol), and stirred 16 h at room temperature (when reactions were slow, the temperature was elevated to 50° C.). The solution was neutralized with 1N HCl (2 mL, 2 mmol) and the organic solvent evaporated to afford an aqueous solution with an insoluble product. If the insoluble was a solid, it was filtered and dried to afford the final product. If the insoluble was an oil, it was extracted with EtOAc (30 mL). The organic solution was separated, washed with water (2×30 mL), dried, filtered, and evaporated to afford the final product.

Example 2

2-{2-methyl-4-[({4-methyl-2-[3-fluoro-4-(trifluoromethyl)phenyl]-1,3-thiazol-5-yl}methyl)sulfanyl]phenoxy}acetic Acid

Intermediate 1

NaHCO$_3$ (2 mmol) was added to a solution of P$_4$S$_{10}$ (0.2 mmol) in toluene (100 mL) and the mixture heated to reflux for ca. 30 min. The substituted benzamide (1 mmol) was added and the reaction stirred at 90° C. for 1 h. The reaction was then evaporated to dryness, treated with brine (100 mL)

and extracted with CH$_2$Cl$_2$ (2×50 mL). The organic phase dried, filtered, and evaporated to afford the final product as a yellow solid (50%). MS m/z 223

Intermediate 2 was reacted with ethyl-2-chloroacetoacetate (1:1 mmol) and the mixture heated to reflux overnight. The reaction was cooled to room temperature and the solvent evaporated. The solid was crystallised from Et$_2$O or hexane to afford the the title compound as an off-white solid (56%). MS m/z 333

Intermediate 3 was reacted with a solution of LiAlH$_4$ at 0° C. The reaction was stirred while it was allowed to warm to rt. After all the starting material had disappeared, the reaction was cautiously treated with water (5 mL) followed by 1N NaOH (10 mL). The mixture was filtered through celite. The filtrate was extracted with CH$_2$CL$_2$ (3×50 mL). The organic phase was dried, filtered and evaporated to afford the title compound as an off-white solid (63%). MS m/z 291

Intermediate 4

To a solution of the Intermediate 3 (1 mmol) and Et3N (2 mmol) in CH$_2$Cl$_2$ (100 mL) at 0° C. was added dropwise methanesulfonyl chloride (1.6 mmol). After 2–4 h the reaction was complete. CH$_2$Cl$_2$ (50 mL) is added and the organic phase washed with a saturated. NaHCO3 solution (2×50 mL), water (2×50 mL), dried, filtered and then evaporated to afford the title compound as a pale yellow solid (100%).

1H-NMR (CDCl3) δ2.40 (s, 3H), 4.70 (s, 2H), 7.55–7.75 (m, 3H).

Intermediate 5

Chlorosulfonic acid (15 mL) was cooled to 0° C. then 10.0 g (0.05M) of ethyl (2-methylphenoxyacetate was added over 10 m. The reaction mixture was stirred at 0–5° C. for 30 m, the bath was removed and stirring continued for 2 h. The reaction mixture was poured into ice, forming a white solid which was washed with ice water and dried under high vacuum affording the title compound (12.846 g, 86%).

Example 2a

Ethyl 2-{2-methyl-4-[({4-methyl-2-[3-fluoro-4-(trifluoromethyl)phenyl]-1,3-thiazol-5-yl}methyl)sulfanyl]phenoxy}acetate Intermediate 5 (4.68 g, 16 mM) was refluxed with 9.6 g of tin powder in ethanol (20 mL) and dioxane/HCl (20 mL). After 3 h the reaction mixture was poured into ice and CH$_2$Cl$_2$ (200 mL) and filtered. The phases were separated and the aqueous layer was extracted 2×50 mL CH$_2$Cl$_2$. The combined organic layers were dried (MgSO$_4$), filtered and evaporated to yield 3.5 g (97%). This material readily forms disulfides and therefore was used immediately. It was dissolved in acetonitrile (50 mL) with intermediate 4 (4.0 g, 14.0 mM) and Cs$_2$CO$_3$ (10.1 g, 31.0 mM) and stirred for 1 h then diluted with ether (200 mL) and water (200 mL). The phases were separated and the organic phase was washed 2× NaOH 0.1N (50 mL), dried (MgSO$_4$), filtered and evaporated to afford crude product (6.57 g,) which was intermediate 54. The crude material was chromatographed CH$_2$Cl$_2$ (100%) to afford the title compound (50%) as a clear oil that solidified on standing.

1H-NMR (CDCl3) δ1.20 (t, 3H), 2.15 (s, 3H), 2.20 (s, 3H), 4.05 (s, 2H), 4.15 (q, 2H), 4.55 (s, 2H), 6.55 (d, 1H), 7.05 (dd, 1H), 7.15 (d, 1H), 7.55 (t, 1H), 7.65 (m, 2H). MS m/z 500 (M+1)

Example 2b

2-{2-methyl-4-[({4-methyl-2-[3-fluoro-4-(trifluoromethyl)phenyl]-1,3-thiazol-5-yl}methyl)sulfanyl]phenoxy}acetic Acid A solution of Example 2a (1 mmol) in THF (10 mL) was treated with 1N LiOH in water (2 mL, 2 mmol), and stirred 16 h at room temperature (when reactions were slow, the temperature was elevated to 50° C.). The solution was neutralized with 1N HCl (2 mL, 2 mmol) and the organic solvent evaporated to afford an aqueous solution with an insoluble product. If the insoluble was a solid, it was filtered and dried to afford the final product. If the insoluble was an oil, it was extracted with EtOAc (30 mL). The organic solution was separated, washed with water (2×30 mL), dried, filtered, and evaporated to afford the final product.

The crude material was precipitated from ether to afford the title compound (81%) as a yellow foam: mp<50° C.

Anal. Calcd. for $C_{21}H_{17}F_4NO_3S_2$: C, 53.50; H, 3.63; N, 2.97; S, 13.60. Found: C53.86; H, 3.63; N, 2.87; S, 13.82. MS m/z 472 (M+1)

INOS Biology

The ability of PPAR delta activators to inhibit the activity and expression of inducible nitric oxide synthase (INOS) was examined using potent, selective PPAR delta agonists, such as (2-{2-methyl-4[({4-methyl-2-[4-(trifluoromethyl) phenyl]-1,3-thiazol-5-yl}methyl)sulfanyl]phenoxy}acetic acid (hereinafter referred to as Compound A, synthesised as described in Example 1) and (2-{2-methyl-4-[({4-methyl-2-[3-fluoro-4-(trifluoromethyl)phenyl]-1,3-thiazol-5-yl}methyl)sulfanyl]phenoxy}acetic acid (hereinafter referred to as Compound B, synthesised as described in Example 2b).

In this assay system, lipopolysaccharide (LPS) was used to induce the expression of INOS in the mouse macrophage cell line, J774. Pre-treatment of J774 cells, with pharmacologically relevant concentrations of PPAR delta agonists, resulted in inhibition of the INOS activity. This reduction in INOS activity correlated with a reduction in LPS-induced INOS mRNA expression.

Measurement of iNOS Activity

Figure 1:
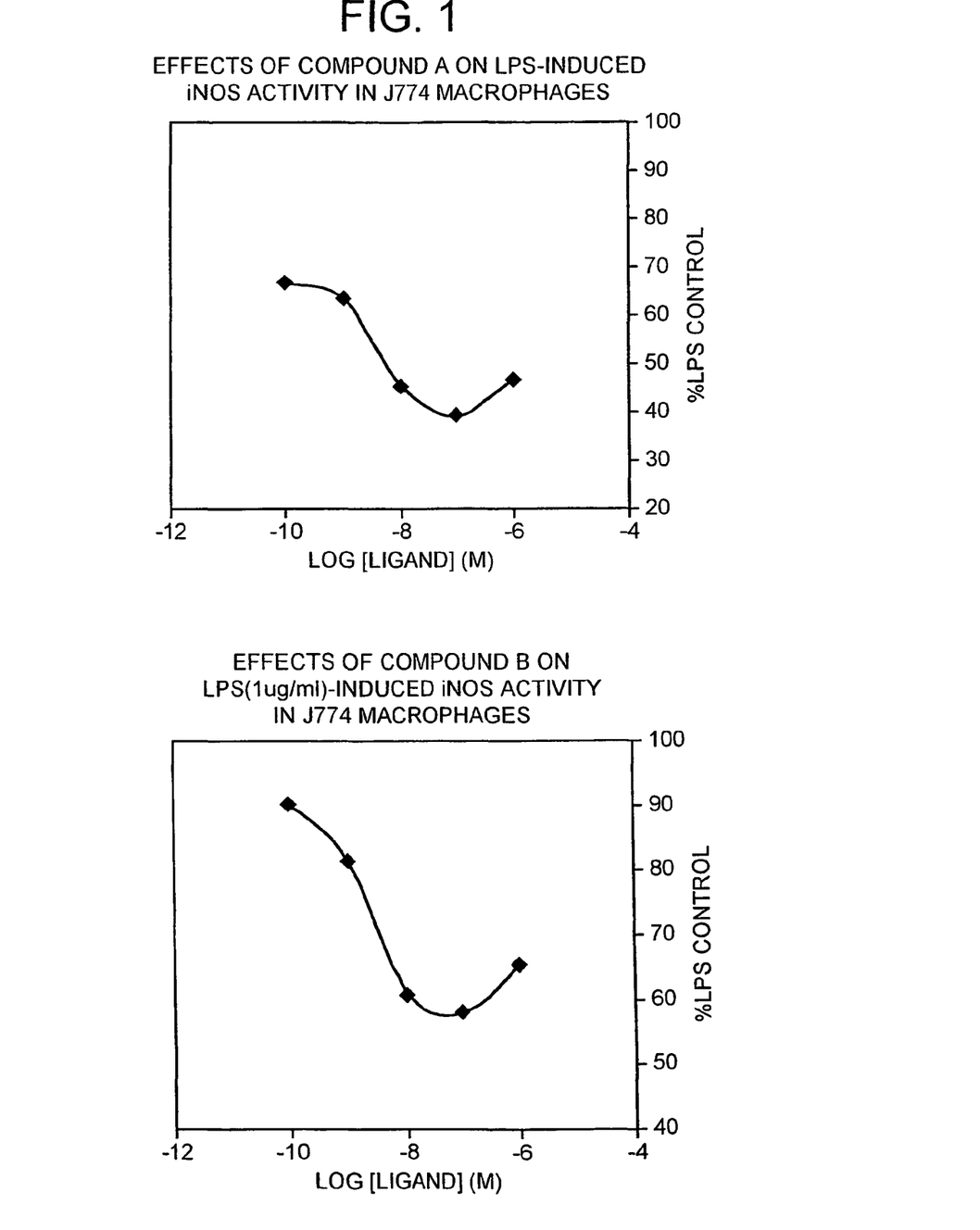
FIG. 1: Shows the effect of PPAR delta agonists on lipopolysaccharide (LPS) induced iNOS activity.

Specifically, LPS-induced INOS activity was measured using the following assay conditions. J774 cells were seeded at a density of 35000–50000 thousand cells per well, in a black, clear-bottomed, 96 well plate, 24 hours prior to use. The cell culture and the drug dilutions were carried out in complete media, which consisted of DMEM (Dulbecco's modification of Eagle's medium) containing foetal calf serum (10%), glutamine (2 mM), penicillin (100 u/ml) and streptomycin (100 µg/ml). The J774 cells were pre-treated with the PPAR delta activators A and B, or vehicle, for 6 hours prior to, and for 24 hours subsequent to the addition of LPS (typically, a concentration of 1 ug/ml of LPS was used). Twenty-four hours after the addition of LPS, INOS activity was measured by the following method. The cell culture media/drug dilutions were removed and the cells washed with D-PBS (Dulbecco's modification of phosphate-buffered saline). The D-PBS was then removed, and replaced with D-PBS containing DAF-2 (4,5-diaminofluorescein; 5 uM) and L-arginine (500 uM). After incubation at 37° C. for 3 hours, fluorescence from each well was measured at an excitation wavelength of 485 nm, and an emission wavelength of 530 nm. The ability of LPS to induce INOS activity, in the presence and absence of PPAR delta activators, was then calculated. Examples of the data obtained are shown in FIG. 1, with the control elevation of INOS activity, induced by LPS, is a response of 100%.

Thus, pre-treatment with Compound A or Compound B, produced a marked inhibition of LPS-induced INOS activity in J774 cells, at sub-nanomolar—nanomolar concentrations.

Measurement of Inhibition of iNOS mRNA

The mechanism, associated with the inhibition of INOS activity by PPAR delta activators, was investigated in greater detail. Specifically, the ability of PPAR delta agonists to inhibit LPS-induced expression of INOS mRNA, in J774 cells was examined. J774 cells were plated in 6 well plates ($10^6$ cells/well), 24 hours prior to use. The cells were pre-treated with PPAR delta activator control media for 6 hours, prior to addition of LPS, which was co-incubated with the PPAR delta activator/control, for a further 24 hours. At the end of this incubation period, the culture medium was removed by aspirating and the cells washed with D-PBS. Following removal of the D-PBS, total cellular RNA was isolated from each sample using a commercially available RNA isolation kit. First strand cDNA synthesis was carried out as per instructions supplied with the AMV reverse transcription (RT) system. An aliquot (1000 ng) of the RNA was added to a mix which contained (final concentrations) $MgCl_2$ (5 mM), Tris-HCl (10 mM; pH 8.8), KCl (50 mM), Triton X-100 (0.1%), dNTP (1 mM), rRNasin (1 U/µl), AMV reverse transcriptase (0.75 U/µl), oligo(dT)$_{15}$ (25 ng/µl). This was incubated in a thermal cycler at 42° C. for 30 minutes, followed by 95° C. for 15 minutes, and, finally, 4° C., until being transferred to a freezer (−20° C.) for storage.

For use in PCR, the following primer sets were used

```
                                       (SEQ ID NO: 1)
Mouse INOS sense       CCCTTCCGAAGTTTCTGGCAGCAGC (SEQ ID NO: 2)
Mouse INOS anti-sense  GGCTGTCAGAGCCTCGTGGCTTTGG (SEQ ID NO: 3)
Mouse GAPDH sense      TGAAGGTCGGTGTGAACGGATTTGGC (SEQ ID NO: 4)
Mouse GAPDH anti-sense CATGTAGGCCATGAGGTCCACCAC
```

PCR was undertaken in a 50 µl reaction volume containing 5 µl of the RT reaction, sense and anti-sense primers for INOS/GAPDH (0.4 pmol/µl), dNTPs (160 µM), KCl (50 mM), Tris-HCl (10 mM; pH 9.0), Triton X-100 (0.1%), $MgCl_2$ (2 mM), and Taq DNA polymerase (0.04 U/µl) (final concentrations). The PCR was carried out in a thermal cycler using the following conditions: 95° C. for 60 s, followed by 28 cycles of 94° C. for 30 s, 55° C. for 60 s, 72° C. for 90 s. Following a final extension step of 72° C. for 5 minutes, the samples were maintained at 4° C., until analysed on an agarose gel. Analysis of sybr-green stained gels, by densitometry, was carried out using a Storm fluorimager system (Molecular Devices).

Figure 2:
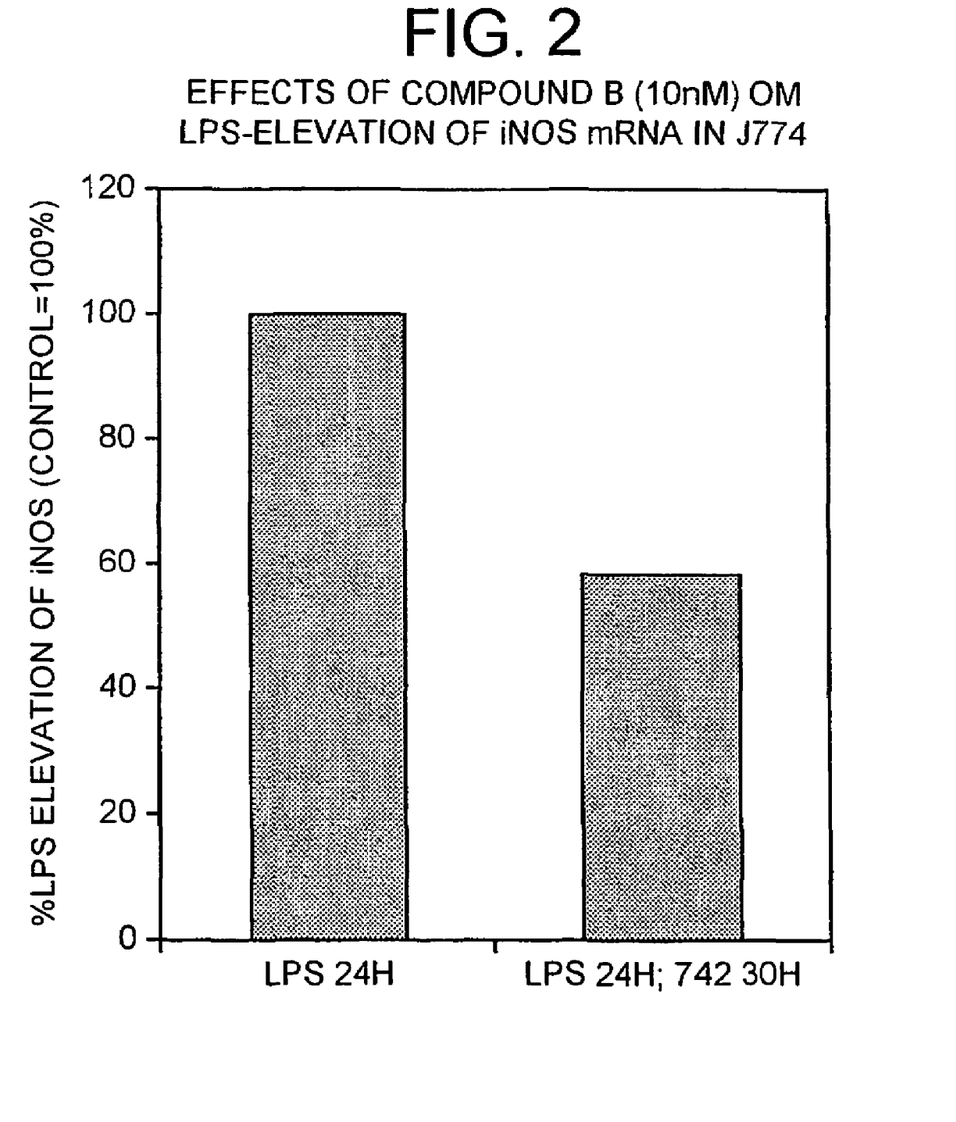
FIG. 2: Shows the effect of a PPAR delta agonist on LPS elevation of iNOS mRNA.

Thus, pre-treatment of J774 cells, with pharmacologically relevant concentrations of PPAR delta activators, resulted in inhibition of LPS (1 µg/ml for data below)-induced INOS mRNA expression. This data is shown in FIG. 2.

Measurement of Inhibition of TNF

The ability of PPAR delta activators to inhibit the expression/secretion of tumour necrosis factor-α (TNF) was also examined. Thus, the ability of PPAR delta activators to inhibit LPS-induced TNF expression correlated well with the inhibitory effects of PPAR delta activators on LPS-induced INOS activation.

Figure 3:
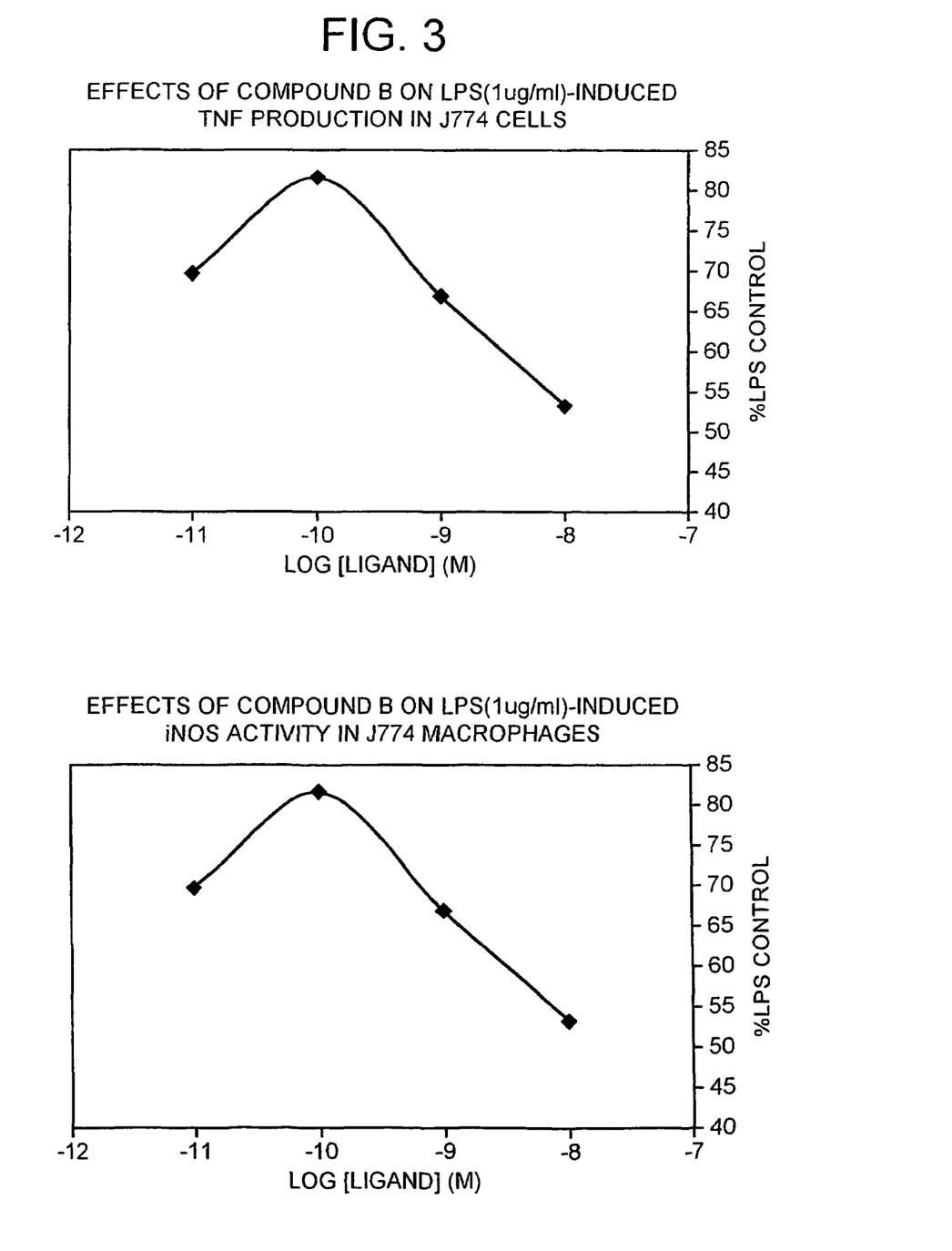
FIG. 3: Shows the effect of a PPAR delta agonist on LPS-induced TNFα expression compound to LPS-induced iNOS activation.

Specifically, LPS-induced INOS activity and expression of TNF was measured using the following assay conditions. J774 cells were seeded at a density of 35000–50000 thousand cells per well, in black, clear-bottomed, 96 well plates. The cell culture and the drug dilutions were carried out in complete media, which consisted of DMEM (Dulbecco's modification of Eagle's medium) containing foetal calf serum (10%), glutamine (2 mM), penicillin (100 u/ml) and streptomycin (100 μg/ml). The J774 cells were pre-treated with PPAR delta activators, or vehicle, for 6 hours prior to, and for 24 hours subsequent to the addition of LPS (typically, a concentration of 1 μg/ml of LPS was used). Twenty-four hours after the addition of LPS, INOS activity was measured by the following method. The cell culture media/drug dilutions were removed for measurement of TNF concentrations, quantified using a commercially available ELISA system. The cells washed with D-PBS. The D-PBS was then removed, and replaced with D-PBS containing DAF-2 (4,5-diaminofluorescein; 5 μM) and L-arginine (500 μM). INOS activity was then measured as described previously. Examples of the data obtained are illustrated in FIG. 3.

The application of which this description and claims forms part may be used as a basis for priority in respect of any subsequent application. The claims of such subsequent application may be directed to any novel feature or combination of features described herein. This may take the form of product, composition, process or use claims and may include, by way of example and without limitation, one or more of the following claims.

The invention claimed is:

1. A method of treating inflammatory diseases or conditions in a human, which comprises the administration of a {2-methyl-4-[4-methyl-2-(4-trifluoromethyl phenyl) thiazol-5-ylmethylthio]phenoxy}-acetic acid.

* * * * *